(12) United States Patent
Feygin

(10) Patent No.: US 6,365,412 B1
(45) Date of Patent: Apr. 2, 2002

(54) CENTRIFUGAL DISPENSER AND METHOD OF USE

(75) Inventor: Ilya Feygin, Mountainside, NJ (US)

(73) Assignee: Pharmacopeia, Inc., Princeton, NJ (US)

( * ) Notice: Subject to any disclaimer, the term of this patent is extended or adjusted under 35 U.S.C. 154(b) by 0 days.

(21) Appl. No.: 09/494,328

(22) Filed: Jan. 28, 2000

(51) Int. Cl.[7] ............................................... G01N 35/00
(52) U.S. Cl. ........................ 436/45; 422/72; 422/100; 436/180
(58) Field of Search ..................... 422/72, 64, 100; 436/180, 45

(56) References Cited

U.S. PATENT DOCUMENTS

| | | | | |
|---|---|---|---|---|
| 3,192,968 A | * | 7/1965 | Baruch et al. | |
| 4,294,127 A | * | 10/1981 | Tomoff | |
| 4,647,432 A | * | 3/1987 | Wakatake | |
| 4,844,868 A | * | 7/1989 | Rokugawa | |
| 5,077,013 A | * | 12/1991 | Guigan | |
| 5,171,532 A | * | 12/1992 | Columbus et al. | |
| 5,310,523 A | * | 5/1994 | Smethers et al. | |
| 5,947,167 A | * | 9/1999 | Bogen et al. | |

* cited by examiner

*Primary Examiner*—Jan Ludlow
(74) *Attorney, Agent, or Firm*—Wayne S. Breyer; Jason Paul DeMont; DeMont & Breyer, LLC

(57) ABSTRACT

An article for dispensing very small volumes of liquid via non touch-off transfer. The article includes a rotator that drives a liquid dispensing system in circular motion at constant rotational speed. The liquid dispensing system has a delivery system that is operatively connected to a dispensing element A small volume of liquid is advanced by the delivery system to the dispensing element. As a consequence of the circular motion, energy is imparted to the liquid causing it to forcibly issue from the dispensing element.

11 Claims, 2 Drawing Sheets

CENTRIFUGAL DISPENSER AND METHOD OF USE

FIELD OF THE INVENTION

The present invention relates to an article for dispensing small volumes of liquid.

BACKGROUND OF THE INVENTION

Pharmaceutical screening of drug candidates, clinical research and applications, genetic research, combinatorial chemistry, analysis and printing, among others, depend on accurate dispensing of very small volumes of liquid. Carrying out methods in such fields using very small volumes of liquid, as opposed to larger volumes, facilitates rapid screening operations, decreases reagent usage and decreases disposal requirements. It is, however, rather difficult to accurately and reliably dispense such small volumes of liquid.

Dispensing liquid volumes within a range of tens of nanoliters to about 2 microliters is particularly problematic. The difficulty lies in overcoming the surface tension between the dispensable liquid and the dispenser. Specifically, the weight of such a small volume of liquid is insufficient to overcome surface tension effects. This difficulty affects the accuracy and repeatability of the dispensing operation.

One method for nano- and micro-volume dispensing is to "push" a small portion of the dispensable liquid out of its dispenser and bring the exposed liquid into contact with a receiver. This method, referred to as "touch-off" transfer, utilizes the surface tension between the exposed liquid and the receiver (or liquid in the receiver) to draw the desired volume of dispensable liquid out of its dispenser. Exemplary touch-off dispensers include capillary tubes, wettable pegs or pins and syringes.

While mechanically simple and inexpensive, touch-off transfer is a relatively slow process. Furthermore, the repeatability and accuracy of touch-off transfer is suspect. In addition, touch-off dispensers may cause undesirable carry-over or cross contamination wherein a substance within the receiver is drawn into or onto the dispenser. To avoid contamination, touchoff dispensers must be cleaned between dispensing cycles, and, in fact, complete replacement of dispensing tips may be required. Moreover, touch-off transfer cannot always be used as it depends on surface and liquid parameters.

In a second method for nano- and micro-volume dispensing, dispensable liquid is forcibly ejected from a dispenser, thereby overcoming surface tension. This method is referred to as "non touch-off" transfer. Exemplary non touch-off dispensers include flow modulators, micrometering pumps and piezo- or thermally-activated liquid ejectors as are often used in print heads. While avoiding some of the problems that plague touch-off dispensers, non touch-off dispensers have other drawbacks. In particular, liquid ejectors are usually restricted to use with a very limited range of volumes and typically require very clean and specially developed fluids. Pumps and flow modulators tend to be slow, have limited reliability and are often incompatible with biochemical or chemical reagents.

As such, there is a need for a dispenser that is capable of dispensing nano- and microvolumes of liquid and that avoids the drawbacks of prior art touch-off and non touch-off dispensers.

SUMMARY OF THE INVENTION

A method and article for dispensing very small volumes of liquid is disclosed. The present dispenser uses non touch-off transfer thereby avoiding the possibility of cross contamination. Yet, it is implemented in a manner that avoids the above-discussed limitations of most prior-art non touch-off dispensers.

In accordance with the present teachings, some embodiments of the present article utilize centrifugal forces to eject liquid volumes in the range of tens of nanoliters to several microliters from a dispensing element. In one embodiment, the present dispenser comprises a rotating element (hereinafter "rotator") that develops and maintains a predetermined speed of rotation. The rotator rotates a rotatable element (hereinafter "rotor"). The rotor contains (1) a dispensing system and (2) a carrier that supports a plurality of liquid receivers.

The dispensing system includes one or more dispensing elements and a device(s) for delivering a desired quantity of liquid to each dispensing element. For example, in one embodiment, the dispensing system comprises a multiplicity of syringe pumps operatively connected to a like number of dispensing needles. Each syringe pump advances a desired volume of liquid from its reservoir to the tip of the communicating needle for dispensing. The volume of liquid is dispensed due to the centrifugal force generated by the rotator. The liquid is dispensed toward a liquid receiver that is disposed near to and facing the syringes.

The carrier that supports the liquid receivers is advantageously advanceable in a predetermined step with reference to the dispensing element (e.g., the needles). This feature allows liquid to be dispensed into each one of a plurality of liquid receivers that are disposed on the carrier. Moreover, in some embodiments, the dispensing elements are movable in a direction perpendicular to the rotating plane and parallel to the axis of rotation in order to align, as required, with each liquid receiver.

DETAILED DESCRIPTION

Figure 1:
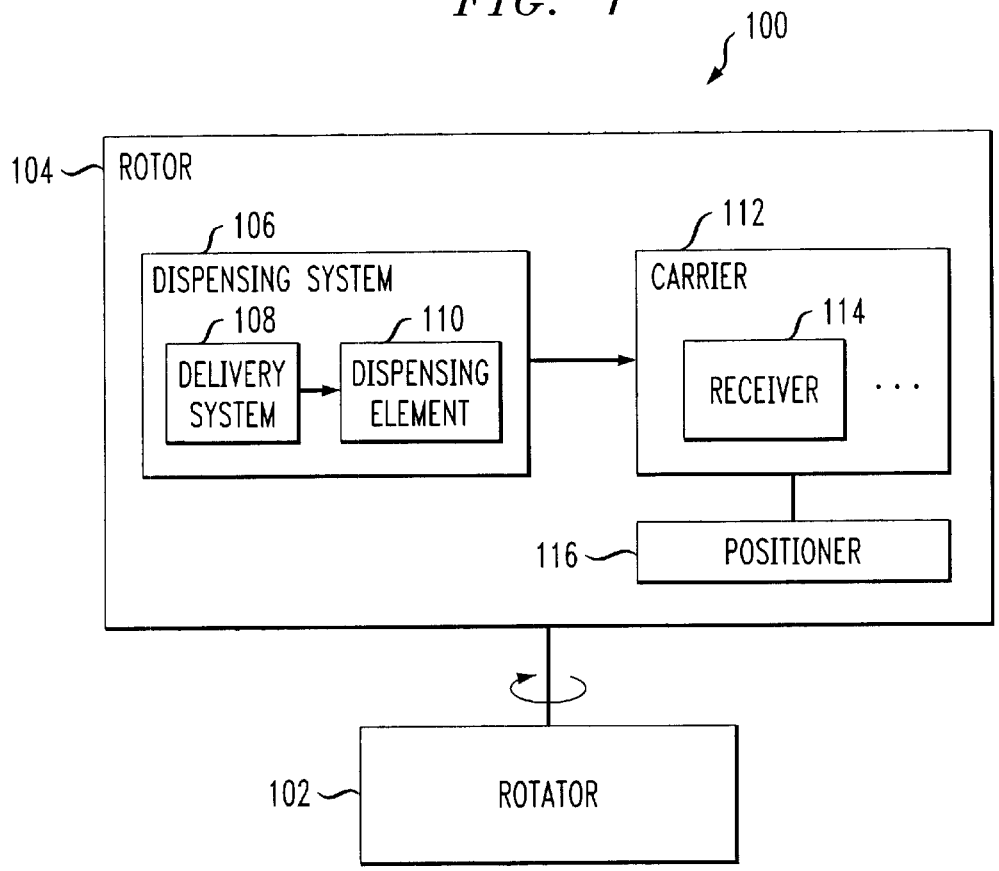
FIG. 1 depicts a block flow diagram of an illustrative embodiment of the present dispensing article.
Figure 2:
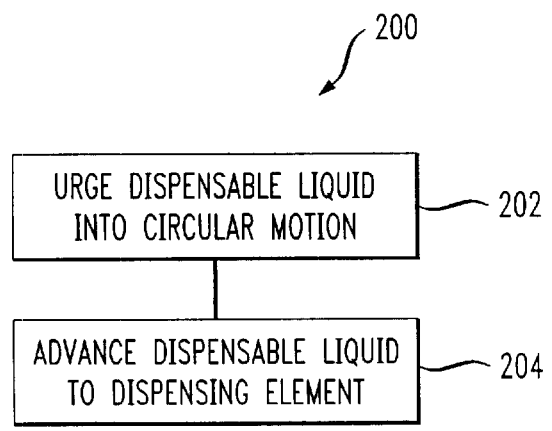
FIG. 2 depicts a method in accordance with the present invention.

As depicted in FIG. 1, dispensing article 100 includes rotator 102 that drives rotor 104 in circular motion at a constant and stable speed (although the speed is adjustable). Rotor 104 contains dispensing system 106 and carrier 112. Dispensing system 106 includes delivery system 108 and dispensing element(s) 110. Delivery system 108 includes a reservoir (not shown) and an arrangement (not shown) for advancing a small, predetermined volume of the liquid from the reservoir to each of dispensing elements 110. Carrier 112 supports a plurality of liquid receivers 114.

In operation, and in accordance with operation 202 of method 200, rotor 104 is driven in circular motion at constant speed by rotator 102. As a consequence, dispensing system 106 and receivers 114 within rotor 104 are likewise driven in circular motion. In accordance with operation 204 of method 200, delivery system 108 delivers a predetermined volume of liquid to dispensing elements 110. The energy imparted from rotator 102 is responsible for forcefully, accurately and repeatably ejecting liquid from dispensing elements 110 toward receiver 114.

Before proceeding further with a description of illustrated embodiments of the inventive concept, it will be useful to consider the "physics" of the present dispensing method.

Centripetal "holding" force F, which is directed towards the center of rotation, is equal to the outward acting "centrifugal" force and is proportional to mass m, tangential velocity V and inversely proportional to the radius R of the rotor:

$$F=(mV^2)/R \quad [1]$$

The force F, which is generated by the rotational motion of rotator 102, provides "potential" energy to the dispensable liquid.

As described later in this Specification, very small conduits or capillaries place delivery system 108 in fluid communication with dispensing elements 110. The "holding" force inside a conduit (ie., the adhesion of liquid to the surface of the conduit) is proportional to the height of capillary column h that can be sustained inside dispensing element 110 with an internal radius r, liquid surface tension τ and liquid density ρ. The height of capillary column h is given by:

$$h=2\tau(r\rho g) \quad [2]$$

where: g is the acceleration due to gravity (9.8 meters per second squared).

Since the adhesion force, represented by the height of a capillary channel, is inversely proportional to acceleration g, the size of the smallest dispensable droplet can be reduced tenfold, for example, by increasing the g-value tenfold. One way to increase "gravity" is to generate an "artificial" gravity by a centrifuge or like device. Substituting F=ma into expression [1] gives:

$$g=V^2/R \quad [3]$$

As "gravity" is artificially increased, the ratio of the capillary force to gravity decreases. As a consequence, a droplet having a much smaller volume (mass) than under the regular free-fall acceleration (1 g=9.8 meters per second squared) can readily overcome adhesion forces and disengage from the outer surface of the dispensing element.

Using expression [3], and assuming that the radius R of a medium size bench-scale centrifuge is 30 centimeters and setting g at (10×g)=98 meters per second squared, then V=5.5 meters per second. Since the exemplary centrifuge has a radius of 30 centimeters, its circumference is about 1.8 meters. Thus, the centrifuge has to rotate at about three revolutions per second or 180 rpm to provide the required velocity and the desired force, which, in this example, is 10 times g.

Thus, the rotational speed of rotor 104 is suitably adjusted to provide sufficient energy to the droplet so that it readily disengages from dispensing element 110. Of course, the rotational speed of rotor 104 is adjusted via the speed of rotator 102. An acceleration of ten times the gravitational force is expected to be sufficient to form and disengage a drop of liquid having a volume as low as tens of nanoliters.

It is expected that in most applications, there will be far fewer dispensing elements 110 than receivers 114 in rotor 104. As such, some embodiments of the present invention advantageously include an arrangement whereby receivers 114 are advanced relative to dispensing elements 110 so that liquid is dispensed to all such receivers. In the illustrative embodiment, such an arrangement is implemented by positioner 116 that is capable of advancing carrier 112 relative to dispensing elements 110 in any predetermined step or series of steps.

By way of illustration, assume that there is a group of eight dispensing elements for dispensing liquid into a plurality of 96-well (8 columns×12 rows) microtitre plates. One possible series of steps would advance carrier 112 in eleven small increments corresponding to the separation between adjacent rows of wells of the microtitre plate, and then advance the carrier in a single larger increment corresponding to the spacing between adjacent microtitre plates. Alternatively, rather than changing the increment to account for the larger spacing between plates, the smaller well-to-well increment can be maintained and the timing of delivery system 108 altered as required.

It will be appreciated that the inventive principle described herein can be realized in many different ways. For example, rotator 102 can be realized as a centrifuge that receives rotor 104. Alternatively, rotator 102 can be realized as a rotating platform or simply a motor that drives rotor 104. Implementing rotator 102 as a centrifuge facilitates placing rotor 104 and its contents under partial vacuum or under an inert atmosphere, as may be desirable depending upon the application.

Similarly, there are a variety of different ways in which power and control can be transferred to rotor 104 to control dispensing system 106 and carrier 112. For example, a battery can be placed in rotor 104 to power the dispensing system and carrier. Alternatively, a rotary transformer with a stationary primary winding and a secondary winding located in rotator 102 can be used to generate power for dispensing system 106 and carrier 112. Optical or RF links can be used to deliver control signals.

Moreover, a wide variety of dispensing systems 106 may be suitably used in conjunction with the present invention. For example, well-known syringe dispensers and valve dispensers are well suited for use in conjunction with the present invention.

Simply put, the manner in which the inventive concept described above is implemented—the equipment used, the way such equipment is arranged, etc.—is a matter of engineering choice. Such details are not addressed herein so that attention can be focused on elements that are germane to an understanding of the present invention. Those skilled in the art can readily implement the teachings disclosed herein in a variety of ways.

Figure 3:
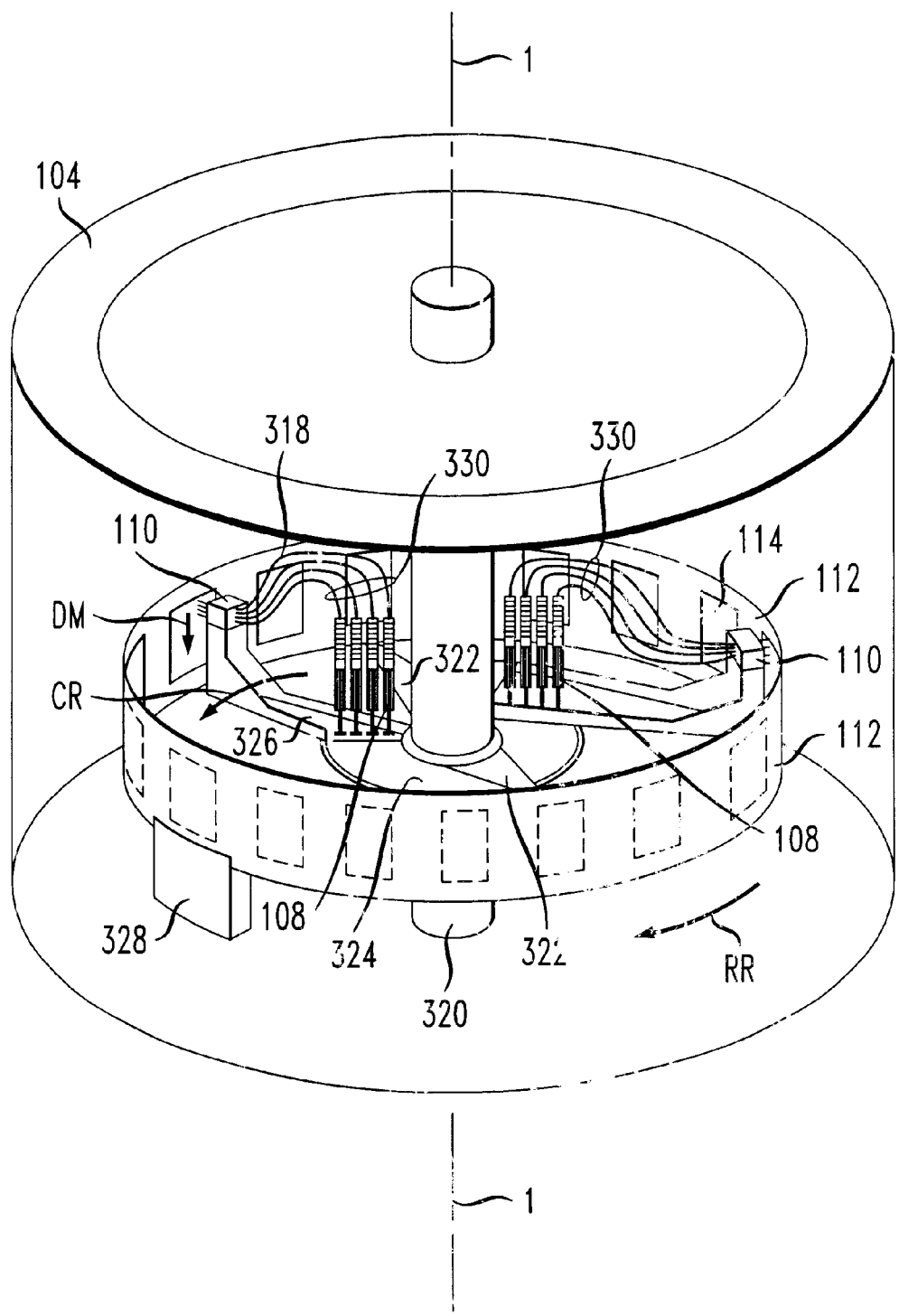
FIG. 3 depicts a rotor, dispensing system and carrier in accordance with the present teachings.

To further illustrate the inventive concept, FIG. 3 depicts an illustrative embodiment of rotor 104, dispensing system 106 and carrier 112. In the embodiment depicted in FIG. 3, rotor 104 is configured as a cylindrical container. Shaft 320 is aligned with axis of rotation 1—1 and rotates with rotor 104. In the illustrated embodiment shaft 320 supports carrier 112 and dispensing system 106.

Carrier 112, which is realized in the illustrated embodiment as a circular member, is supported by spokes 322 that engage shaft 320. Incremental positioner 328 is operative to sequentially advance the carrier so that the plurality of receivers 114 disposed on carrier 112 are sequentially presented to dispensing elements 110 to receive liquid. Arrow RR indicates the rotation of rotor 104, and arrow CR depicts the incremental advancement of carrier 112. It should be understood that the rotational directions are arbitrary; they are depicted as being opposed to emphasize that carrier 112 is advanced independently of rotor 104 (although carrier 112 is driven by rotator 102).

Platform 324 is rigidly attached to shaft 320. Delivery system 108, which is realized in the illustrated embodiment as two groups of four syringe pumps each, is disposed on platform 324. Arms 326 depend from platform 324 and extend toward carrier 112. Dispensing elements 110, implemented in the illustrative embodiment as two groups of four needles each, depend from the distal end of arms 326. Small diameter conduits or capillaries 330 place delivery system 108 in fluid communication with dispensing elements 110.

Dispensing elements 110 are advantageously operable to move orthogonally to the rotating plane and parallel to axis 1—1 along direction DM in order to align with receivers 114 as required. In some embodiments, a "wind deflector," not shown, is disposed on or near to dispensing elements 110. The wind deflector shields dispensed liquid from the "wind" that is generated by rapidly rotating rotor 104.

In operation, rotor 104 and the contents thereof are urged into circular motion by rotator 102 (not shown in FIG. 3). A rotational speed that is determined to impart sufficient energy to the dispensable liquid is attained and maintained. In response to a control signal (controller not depicted), each of the syringes comprising delivery system 108 advances, via positive displacement of the piston in each syringe, a predetermined volume of liquid through each of conduits 330 toward dispensing elements 110. Due to the energy imparted to the liquid, the liquid is readily dispensed from dispensing elements 110. Dispensing elements 110 are advantageously disposed very close to receivers 114 so that liquid issuing from the dispensing elements is accurately delivered to the receivers.

After the liquid is dispensed, incremental positioner 328 advances carrier 112 for delivering liquid to the next receiver (e.g., next group of wells, next microtitre plate, next biochip, etc.). The process then repeats wherein additional liquid is advanced and dispensed.

It is to be understood that the above-described embodiments are merely illustrative of the invention and that many variations can be devised by those skilled in the art without departing from the scope of the invention. It is therefore intended that such variations be included within the scope of the following claims and their equivalents.

I claim:

1. A liquid dispenser comprising:
    a rotator;
    a rotor that is rotated into continuous circular motion by said rotator;
    a dispensing system disposed within said rotor, said dispensing system having:
        dispensing elements that dispense liquid using rotational energy imparted by said rotor; and
        a delivery system that is in fluid communication with said dispensing elements, wherein said delivery system advances liquid to said dispensing elements via applied non-centrifugal pressure; and
    a carrier disposed within said rotor, wherein said carrier supports liquid receivers in spaced-apart and close spatial relation to said dispensing elements to receive said liquid therefrom.

2. The liquid dispenser of claim 1 further comprising an incremental positioner that incrementally advances said carrier relative to said dispensing elements.

3. The liquid dispenser of claim 1 wherein said carrier comprises a circular band, the center of which is aligned with a rotational axis of said rotor.

4. The liquid dispenser of claim 1 wherein said rotor has a shaft aligned with a rotational axis thereof, and wherein said dispensing system and said carrier are mechanically linked to said shaft.

5. The liquid dispenser of claim 1 wherein said delivery system comprises a plurality of syringe pumps.

6. The liquid dispenser of claim 5 wherein said dispensing elements comprise a plurality of needles.

7. The liquid dispenser of claim 1 wherein said dispensing elements are movable in a direction that is perpendicular to a plane of rotation of said rotor and parallel to an axis of rotation of said rotor.

8. A method comprising:
    moving liquid in a circular motion thereby imparting rotational energy to said liquid;
    advancing said liquid to a first plurality of dispensing elements via applied non-centrifugal pressure; and
    dispensing said liquid to a second plurality of receivers using said rotational energy of said liquid.

9. The method of claim 8 further comprising sequentially advancing said receivers past said dispensing elements.

10. The method of claim 8 further comprising moving said dispensing elements in a direction that is perpendicular to a plane of rotation of said liquid.

11. The method of claim 8 wherein said liquid is moved at a constant rotational speed.

\* \* \* \* \*